(12) United States Patent
Mohamed et al.

(10) Patent No.: US 8,060,186 B2
(45) Date of Patent: Nov. 15, 2011

(54) SYSTEM AND METHOD FOR INTRAOPERATIVE GUIDANCE OF STENT PLACEMENT DURING ENDOVASCULAR INTERVENTIONS

(75) Inventors: Ashraf Mohamed, Houston, TX (US); Chenyang Xu, Allentown, NJ (US); Frank Sauer, Princeton, NJ (US); Marcus Pfister, Bubenreuth (DE); Andrew F Hall, St. Charles, MO (US); Klaus Klingenbeck-Regn, Nürnberg (DE)

(73) Assignee: Siemens Aktiengesellschaft, München ( * ) Notice: Subject to any disclaimer, the term of this patent is extended or adjusted under 35 U.S.C. 154(b) by 849 days.

(21) Appl. No.: 12/031,787

(22) Filed: Feb. 15, 2008

(65) Prior Publication Data
US 2009/0088830 A1    Apr. 2, 2009

Related U.S. Application Data

(60) Provisional application No. 60/890,036, filed on Feb. 15, 2007.

(51) Int. Cl.
*A61B 5/05* (2006.01)
(52) U.S. Cl. ............ 600/427; 600/424; 623/1.1
(58) Field of Classification Search .......... None
See application file for complete search history.

(56) References Cited

U.S. PATENT DOCUMENTS 6,733,489 B2 * 5/2004 Nutting et al. .......... 604/529
2006/0184066 A1   8/2006 Karmonik et al.

OTHER PUBLICATIONS

Penney, G., "Registration of Tomographic Images to X-ray Projections for Use in Image Guided Interventions", Computational Imaging Science Group, Division of Radiological Sciences and Medical Engineering, Guy's, King's and St. Thomas' School of Medicine, King's College London, Dec. 1999.

* cited by examiner

*Primary Examiner* — Long V. Le
*Assistant Examiner* — Nicholas Evoy
(74) *Attorney, Agent, or Firm* — Donald B. Paschburg; F. Chau & Associates, LLC

(57) ABSTRACT

A method for guiding stent deployment during an endovascular procedure includes providing a virtual stent model of a real stent that specifies a length, diameter, shape, and placement of the real stent. The method further includes projecting the virtual stent model onto a 2-dimensional (2D) DSA image of a target lesion, manipulating a stent deployment mechanism to navigate the stent to the target lesion while simultaneously acquiring real-time 2D fluoroscopic images of the stent navigation, and overlaying each fluoroscopic image on the 2D DSA image having the projected virtual stent model image, where the 2D fluoroscopic images are acquired from a C-arm mounted X-ray apparatus, and updating the projection of the virtual stent model onto the fluoroscopic images whenever a new fluoroscopic image is acquired or whenever the C-arm is moved, where the stent is aligned with the virtual stent model by aligning stent end markers with virtual end markers.

24 Claims, 8 Drawing Sheets

SYSTEM AND METHOD FOR INTRAOPERATIVE GUIDANCE OF STENT PLACEMENT DURING ENDOVASCULAR INTERVENTIONS

CROSS REFERENCE TO RELATED UNITED STATES APPLICATIONS

This application claims priority from "Intraoperative Guidance for Stent Placement during Endovascular Interventions via X-Ray Fluoroscopy and Image Overlay", U.S. Provisional Application No. 60/890,036 of Mohamed, et al., filed Feb. 15, 2007, the contents of which are herein incorporated by reference.

TECHNICAL FIELD

This disclosure is directed to the use of X-ray C-arm systems in interventional radiology and cardiology, and in particular in guiding stent placement during procedures for treating blood vessel stenosis and aneurysms.

DISCUSSION OF THE RELATED ART

X-ray C-arms are routinely used in medicine to acquire images for diagnostic assessment of a patient's vascular structures, and for real-time guidance of interventional therapeutic procedures such as stent placement or coiling of aneurysms.

Angiograms are 2-dimensional (2D) X-ray projection images of vascular structures filled with a contrast agent, which is typically injected intra-arterially through a catheter. Digital subtraction angiography (DSA) subtracts two X-ray images, one with and one without contrast injection. The background anatomy cancels out, and the blood vessels into which contrast flows are highlighted. Three dimensional (3D) angiograms can be obtained by rotating the X-ray C-arm around the patient's body, acquiring a set of angiograms as 2D projection images during the rotational run, and then reconstructing a 3D volume image from these set of projections.

Fluoroscopic images are low dose X-ray projection images that are acquired to guide and monitor the progress of an interventional procedure in real-time, e.g. to observe the progress of a guidewire, a catheter insertion, a stent deployment, etc.

An aneurysm is a bulge in a blood vessel. It bears the medical risk of vessel rupture leading to internal bleeding, and can cause the death of the patient. Brain aneurysms are usually treated with stents, wire coils, or glue, with the intention to form a blood clot in the aneurysm that relieves the pressure against the aneurysm's wall. A stent is sometimes used as an adjunct for the placement of coils to prevent the protrusion of coils into the parent artery. Coils protruding into an artery may cause the formation of a blood clot. Aneurysms requiring the use of a stent are typically those with a neck wide enough to allow coils inserted into the aneurysm to protrude inside the parent vessel.

Stenosis is a narrowing of a blood vessel that is typically induced by atherosclerotic disease. Arterial stenosis of major blood vessels supplying the brain, such as the internal carotid artery, reduces blood flow to the brain and may lead to significant neurological and functional deficits. Stenosis is usually treated via the deployment of a stent inside the lesion in an attempt to increase the diameter of the blood vessel and improve blood flow.

For each individual lesion to be treated by a stent, the physician needs to determine the length, diameter, and type of stent to use. Proper planning for each case is necessary for achieving the goals of stenting while avoiding complications that may affect the long or short term outcome of the procedure. For example, using a shorter stent than necessary may require the deployment of an additional stent to provide full coverage of the lesion. On the other hand, a stent that is longer than necessary may increase the risk of future blood vessel stenosis/restenosis.

Traditionally, stent placement planning is done on 2D angiography images. The physician measures the vessel and the aneurysm dimensions on the 2D image and determines the dimensions of the stent to use. Measurements based on 2D images may, however, suffer from inaccuracies due to the so-called foreshortening effect. Software tools for stent planning based on the 3D geometry of the blood vessels have recently been proposed and some are available on today's angiographic workstations. Some of these tools rely on 3D reconstructions of the blood vessels from two or more angiographic 2D projections (e.g., IC3D by Siemens Medical Solutions). Other tools rely on 3D DSA images for knowledge of the vessel geometry. For example, a virtual stent planning software, such as that disclosed in United States Patent Application Publication No. 2006/0184066 "Method for aiding stent-assisted coiling of intracranial aneurysms by virtual parent artery reconstruction" of Karmonik, et al., the contents of which are herein incorporated by reference in their entirety, can allow a physician to experiment with various stent lengths and diameters to visualize the stent inside the blood vessel geometry depicted via 3D DSA.

A stent is typically available from the manufacturer as a collapsed thin cylinder enclosed within a sheath or sleeve. Some stents are balloon-expandable and others are self-expandable. Radio-opaque markers are usually present at the ends of the stent to allow the physician to position it with respect to the lesion (e.g. an aneurysm or stenosis) under fluoroscopic guidance during treatment. Several markers are present at each end of the stent, however when a stent is collapsed and enclosed in its sleeve, the markers at each end appear as a single dark spot on fluoroscopic images.

Although state of the art tools can assist in planning stent deployment procedures, these tools do not provide intra-operative guidance to assist in the placement of a stent at this planned position. Inaccurate deployment of a stent has the potential of causing undesirable complications similar to those involved in improper planning—namely, the need for the placement of an additional stent, or the risk of future blood vessel stenosis.

SUMMARY OF THE INVENTION

Exemplary embodiments of the invention as described herein generally includes methods and systems for intraoperative guidance of stent placement during endovascular interventions. According to an embodiment of the invention, a mathematical and visualization approach superimposes graphical depictions of a virtual endovascular stent on C-arm angiographic and fluoroscopic images for stent placement planning and guidance during an endovascular procedure.

According to an aspect of the invention, there is provided a method for guiding stent deployment during an endovascular procedure, the method including providing a virtual stent model of an real stent that specifies a length, diameter, shape, and placement location of the real stent, where the stent includes radio-opaque end markers, and the virtual stent model includes virtual end markers that are projected onto the fluoroscopic images, projecting an outline and shape taken from the virtual stent model onto a 2-dimensional (2D) DSA image of a target lesion, manipulating a stent deployment mechanism to navigate the real stent to the target lesion while simultaneously acquiring real-time 2D fluoroscopic images of the stent navigation, and overlaying each fluoroscopic image on the 2D DSA image having the projected virtual stent model image, where the 2D fluoroscopic images are acquired from a C-arm mounted X-ray apparatus, and updating the projection of the virtual stent model onto the fluoroscopic images whenever a new fluoroscopic image is acquired or whenever the C-arm is moved, where the stent is aligned with the virtual stent model by aligning the stent end markers with the virtual end markers.

According to a further aspect of the invention, the virtual stent model is created using a 3-dimensional (3D) image of a target blood vessel lesion, and determining a length, diameter type, and placement location of a planned stent using the 3D image.

According to a further aspect of the invention, the 3D image of the target lesion is created by constructing a 3-dimensional (3D) digital subtraction angiography (DSA) image of the target blood vessel lesion, where the 3D DSA image is constructed from a plurality of 2D DSA images acquired at different orientations with respect to the target lesion.

According to a further aspect of the invention, the 3D image of the target lesion is one of a magnetic resonance image and a computed tomography image, and further comprising registering the 3D image of the target lesion to a 3D DSA image of the target lesion.

According to a further aspect of the invention, projecting the virtual stent model onto a 2D DSA image comprises determining 2D coordinates u, v of the virtual stent model in the 2D DSA image from an equation $$\begin{bmatrix} \alpha u \\ \alpha v \\ \alpha \end{bmatrix} = P \cdot \begin{bmatrix} x \\ y \\ z \\ 1 \end{bmatrix},$$

where and P is a 3×4 matrix with 10 degrees of freedom obtained from knowledge of design parameters of the C-arm, system calibration procedure, and a location of the C-arm, (x, y, z) is a point in the 3D image, and $\alpha$ is a scalar determined by specifying P and (x, y, z).

According to a further aspect of the invention, the method includes deploying the stent, when the stent is aligned with the virtual stent model in the fluoroscopic images.

According to a further aspect of the invention, projecting the virtual stent model onto a 2D DSA image comprises representing the virtual stent model by a centerline and a plurality of spaced perpendicular lines whose length is about equal to a diameter of expansion of the stent at a location of each the perpendicular line.

According to a further aspect of the invention, an intensity $I_o$ of the projected virtual end marker is $I_o = I_{max} + I_{min} - I_i$, where $I_{max}$ and $I_{min}$ are the minimum and maximum intensity values of the display monitor, respectively, and $I_i$ is the intensity of the pixel underlying the projected virtual end marker.

According to another aspect of the invention, there is provided a program storage device readable by a computer, tangibly embodying a program of instructions executable by the computer to perform the method steps for guiding stent deployment during an endovascular procedure.

DETAILED DESCRIPTION OF EXEMPLARY EMBODIMENTS

Figure 1A:
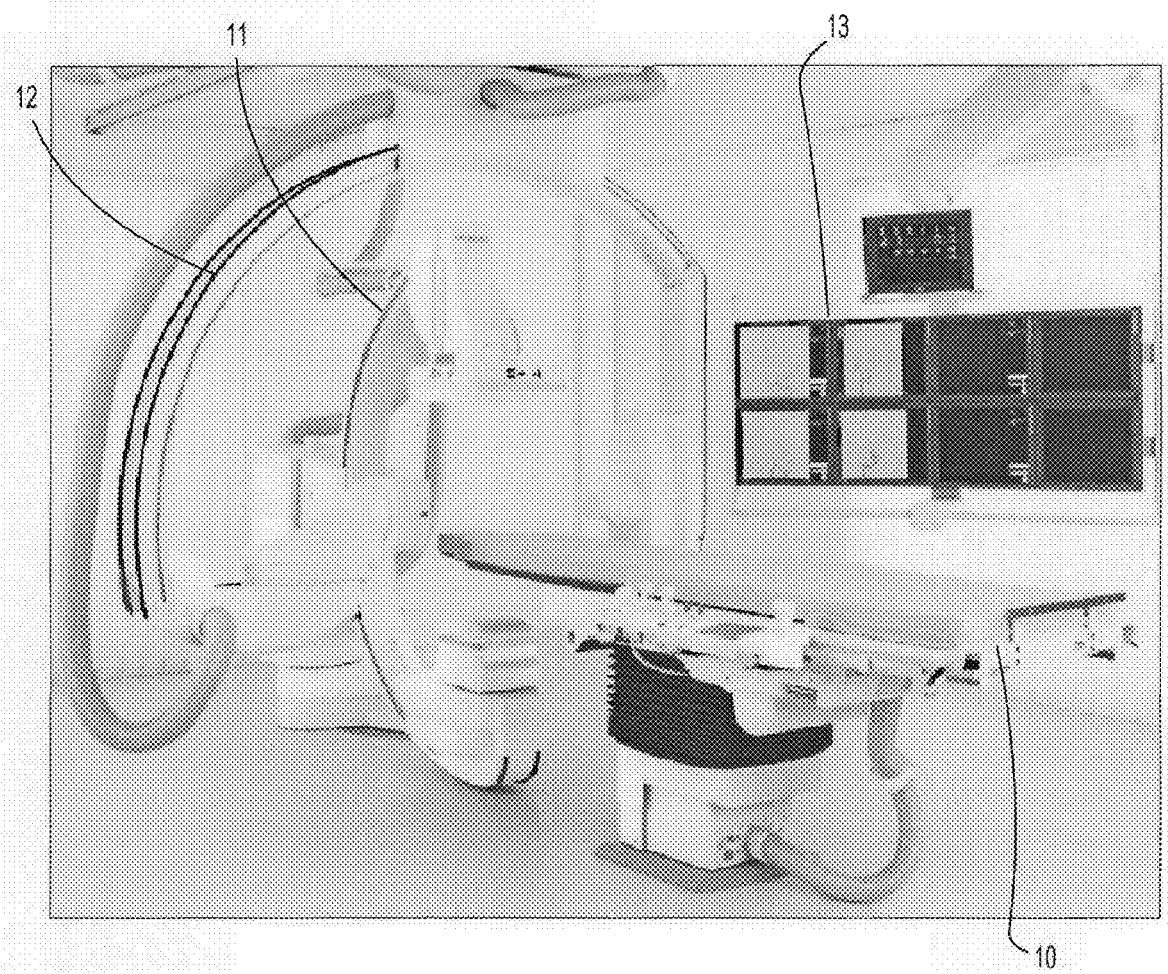
FIGS. 1(a)-(c) illustrate an exemplary biplane angiography system, according to an embodiment of the invention.

Exemplary embodiments of the invention as described herein generally include systems and methods for intraoperative guidance of stent placement during endovascular interventions. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Figure 1B:
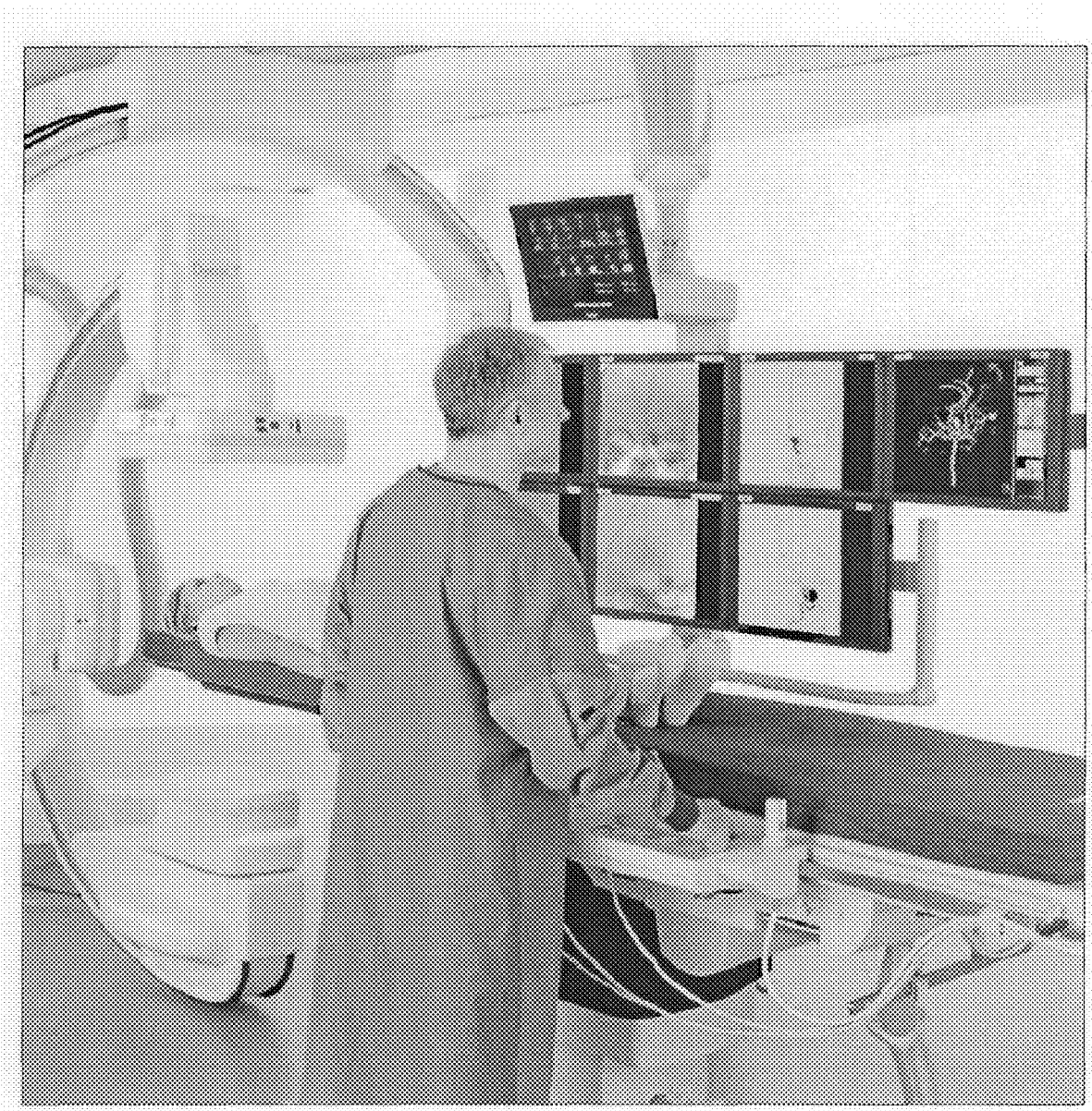
Figure 1C:

An exemplary biplane angiography system is illustrated in FIGS. 1(a)-(c). The angiography suite includes a control room that is isolated by leaded glass from the room with the C-arms and patient. The workstation sits in the control room. An exemplary workstation is a personal computer system. FIG. 1(a) shows the angiography room including a patient table 10, two C-arms 11 and 12 and monitors 13. FIG. 1(b) shows the setup of FIG. 1(a) with a patient on the table and a physician. FIG. 1(c) is a view to the inside of the angiography from the control room, with the workstation's monitors in the foreground. Note that other embodiments of the invention can be used with monoplane systems as well as biplane systems.

According to an embodiment of the invention, the output of an endovascular stent planning session is the required stent type, dimensions, shape and location in relationship to the lesion. Therefore at the end of a planning session it should be possible to fully create a virtual model of the stent by specifying its configuration in 3D space. Through the knowledge of the projective geometry of the C-arm system used to acquire the images, an embodiment of the invention allows the overlay of this 3D model of the virtual stent, or any part thereof, on any 2D image acquired by the fluoroscopy system, at any orientation, pan or zoom factor of the C-arm.

The graphical overlay of the virtual stent model on a two dimensional image provides the physician with two functions. First, it allows the physician to check and revise the results of the stent planning through the overlay of the stent on 2D DSA images. This is useful since stent deployment is usually performed under guidance of a composite image formed of the superposition of a roadmap image derived from DSA and a fluoroscopy image. Second, an embodiment of the invention can superimpose the planned stent end positions on the fluoroscopic image where they can be directly compared to the position of radio-opaque markers at both ends of a real stent. This provides guidance to the physician who is then able to navigate the stent deployment mechanism until the planned position is reached with high accuracy.

Figure 2:
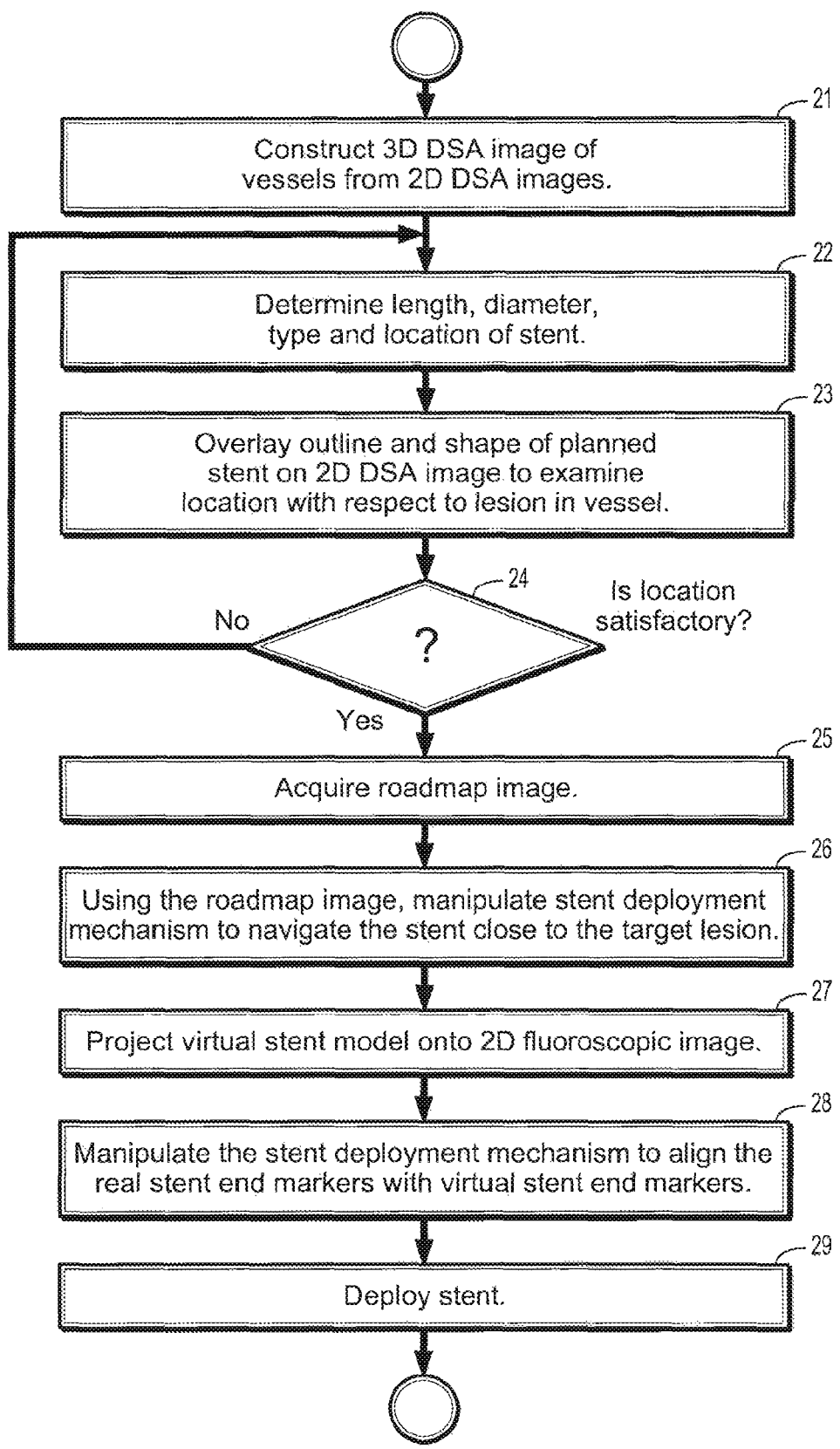
FIG. 2 is a flow chart of an interoperative guidance method according to an embodiment of the invention.

FIG. 2 is a flow chart of an interoperative guidance method according to an embodiment of the invention. Referring now to the figure, the steps involved are as follows. First, at step 21, a 3D DSA image of a patient's contrast-enhanced blood vessels is constructed from 2D DSA images obtained via rotation of the X-ray C-arm around the patient. Next, at step 22, in a stent planning session, a physician loads the 3D DSA image onto an angiography workstation and uses stent planning software to determine the length, diameter, type and location of the stent. Stent planning software is typically not provided by the stent vendors, but is rather a separate product that available for imaging systems from third party vendors. One example of such planning software is disclosed in the aforementioned Karmonik published patent application. The output of the planning software is a virtual planned stent that can be saved in a computer file on the workstation. The virtual stent includes virtual end markers that correspond to the actual stent markers.

In other embodiments of the invention, it is possible that stent planning may be performed on a 3D image from another imaging modality such as magnetic resonance imaging (MRI), or computed tomography (CT), not just a 3d dsa IMAGE. In these cases, the images are typically acquired before the aneurysm/stenosis treatment procedure in the angiography suite. In that case, the 3D virtual stent model is based on that other modality, but this model is registered with the 2D fluoroscopy images via one of a number of ways including 3D/3D registration involving 3D DSA as an intermediate step, or direct image-based 3D/2D registration.

At step 23, the physician can use an embodiment of the invention to overlay the outline and shape of the virtual planned stent on any 2D DSA image acquired for the lesion and saved on the angiography workstation. This allows the physician to examine the virtual planned stent in relationship to the lesion in C-arm projections at various orientations that are used during the placement of the stent. If, at step 24, the location of the stent is unsatisfactory on the DSA images, the physician can return to step 22 and iteratively revise the location of stent using the stent planning software. At the end of step 23, the planned location and configuration of the stent in three dimensions is fully specified.

At step 25, the physician acquires a roadmap image using DSA to aid in navigating the actual stent to the target, and at step 26 manipulates the stent deployment mechanism to navigate the actual stent until it reaches the general area of the target lesion. On the fluoroscopic images, the stent is identified by radio-opaque markers at both ends. Although in some embodiments of the invention the roadmap image can be the same as the DSA image that is used for planning, in other embodiments, the DSA roadmap image is created on the spot after planning is done and when the doctor is inside the interventional room and navigating the catheter or stent deployment system through a patient's vessels.

Using knowledge of the projective geometry of the C-arm system, described below, and given the planned stent marker locations obtained from step 22, the virtual stent markers are projected at step 27 onto the fluoroscopic image displayed on the live monitor inside the control room of the angiography suite. The physician can obtain this superimposition of the virtual stent markers on the live fluoroscopic images at any angle, pan, or zoom factor for the C-arm. The location of the virtual stent markers are automatically updated whenever the physician acquires a new image or moves the C-arm. The projective geometry of the C-arm is described below. The shape and intensity of the projected stent and markers are also described below.

Finally, at step 28, the physician manipulates the stent deployment mechanism to align the real stent end markers with the virtual stent end markers projected on the fluoroscopic image. When the alignment is satisfactory, the physician at step 28 deploys the stent according to the method described by the stent manufacturer.

C-Arm Calibration

An invention according to an embodiment of the invention makes use of knowledge of the projective geometry of a fluoroscopic C-arm to superimpose stent planning information derived from 3D DSA images onto the two dimensional fluoroscopic images.

Let the Cartesian coordinates of a point in 3D space be given by the triplet (x, y, z) and the let the image coordinates of the same point be (u, v) in pixels. The relationship between the two sets of coordinates is given by:

$$\begin{bmatrix} \alpha u \\ \alpha v \\ \alpha \end{bmatrix} = P \cdot \begin{bmatrix} x \\ y \\ z \\ 1 \end{bmatrix},$$

where α is a scalar and P is a 3×4 matrix with 10 degrees of freedom. The parameters of P may be obtained through knowledge of the geometric design parameters of the C-arm, system calibration procedure, and the location of the C-arm. The matrix P is a product of two matrices: I×T. The matrix I is a 3×3 matrix that embodies the intrinsic parameters of the C-arm, which are determined via the calibration procedure and knowledge of the some system parameters, such as the relationship of the X-ray source to the detector. The matrix T is a 3×4 matrix that is a coordinate transformation matrix that depends on the C-arm angles, of which there are two, and the translation of the C-arm with respect to a fixed coordinate system. The constant α is determined as the 3rd coordinate on the left hand side of the equation. Knowing P and the (x, y, z) coordinates of a 3D point, everything on the left hand side can be determined. The coordinates u and v can then be obtained by dividing the first and second components of the left hand side vector by α. In other words, after the left hand side is determined, divide the first component by the 3rd component to get u and divide the second component by the third to get v. Once the parameters of P are obtained, the 3D DSA image can be registered to the 2D fluoroscopic image. There are many 3D to 2D registration methods known in the art. A review of many such methods can be found in G. P. Penney, "Registration of Tomographic Images to X-ray Projections for Use in Image Guided Interventions," Phd thesis, University College London, CISG, Division of Radiological Sciences, Guy's Hospital, King's College London, London SE1 9RT England, 2000, the contents of which are herein incorporated by reference in their entirety.

Display of Planned Stent on 2D DSA Images

Figure 3:
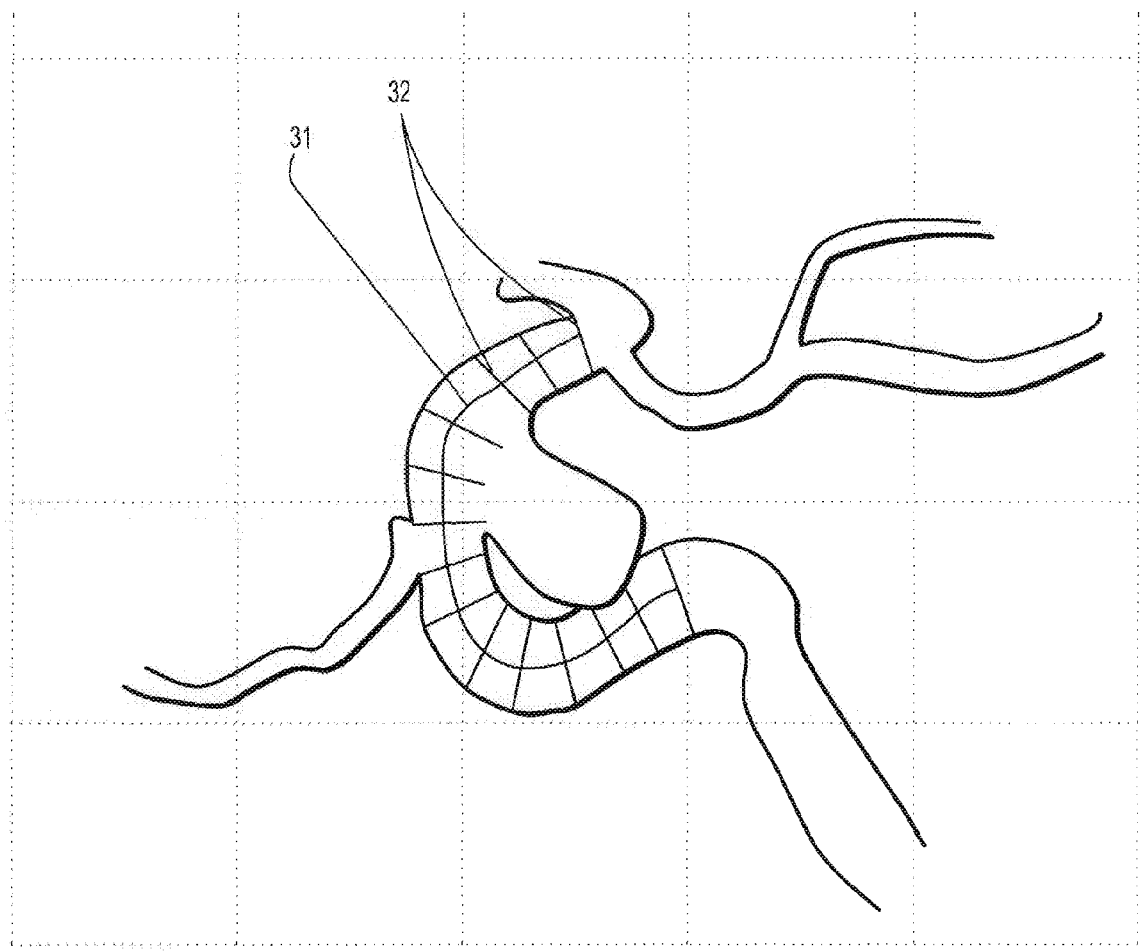
FIG. 3 illustrates a virtual stent superimposed on a 2D image display, according to an embodiment of the invention.

According to an embodiment of the invention, to simplify the display of a virtual stent on a 2D plane, it is depicted as a series of lines that are perpendicular to the stent centerline. FIG. 3 illustrates a virtual stent superimposed on a 2D image display with centerline 31 and perpendicular lines 32. For the sake of clarity, only two such perpendicular lines are indicated by the reference number. The length of each line is equal to the diameter of expansion of the stent at that location.

Figure 4:
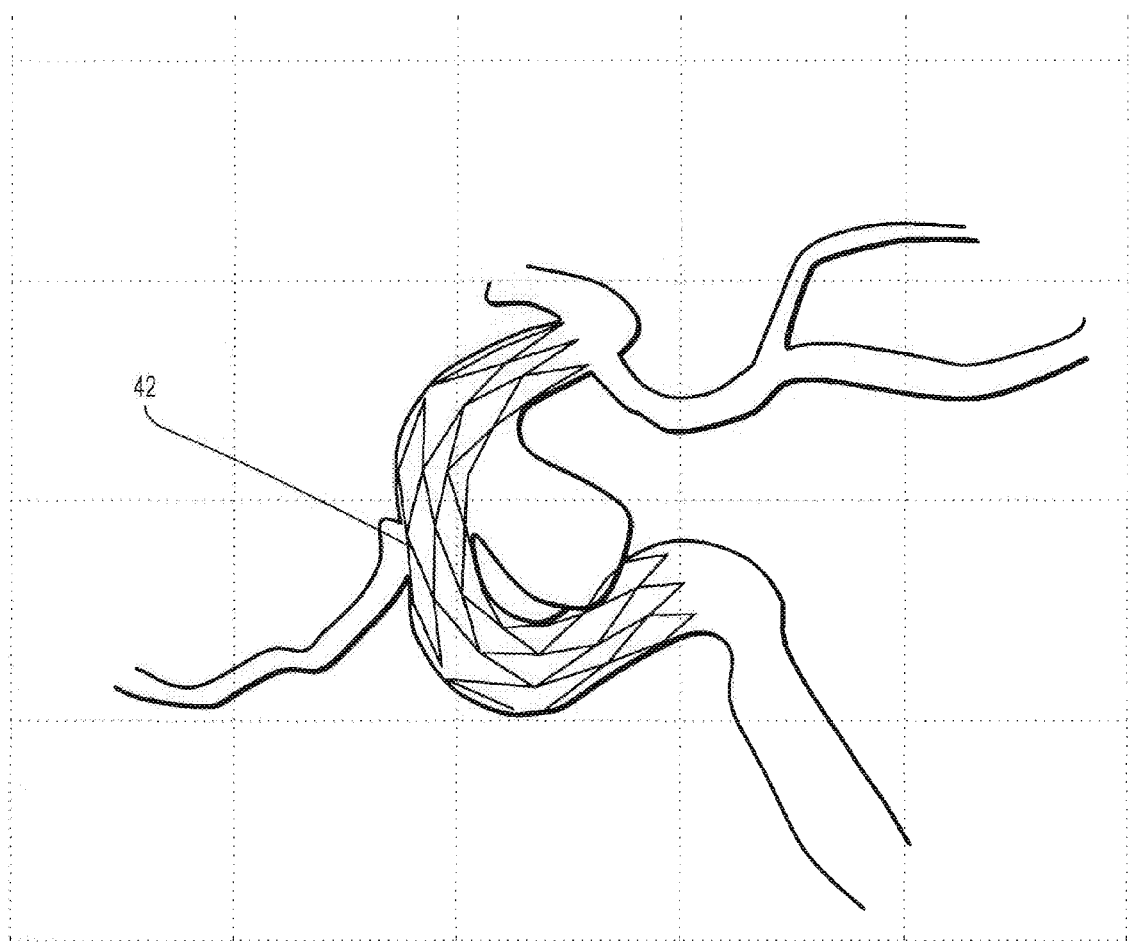
FIG. 4 illustrates a stent 41 superimposed on a DSA image of a lesion, according to an embodiment of the invention.

In general, a 2D DSA image contains either high intensity pixels (background) or dark low intensity pixels (blood vessels filled with contrast). Since most angiography workstations allow the use of colors on display monitors, according to an embodiment of the invention, the stent is superimposed on the DSA image via a non grayscale color such as the color red. FIG. 4 illustrates a stent 41 superimposed on a DSA image of a lesion. The display of the superimposition need not be restricted to a colored stent. For example, in other embodiments of the invention, a stent may also be displayed in a bright white color, which will make it visible on the dark vessels.

Display of the Planned Stent Marker Locations on Fluoroscopy Images

Navigation of a stent to its planned location is performed under guidance of fluoroscopic images. During navigation, the roadmap image is typically superimposed on the fluoroscopy image to visualize the blood vessels and the target lesion.

Figure 5:
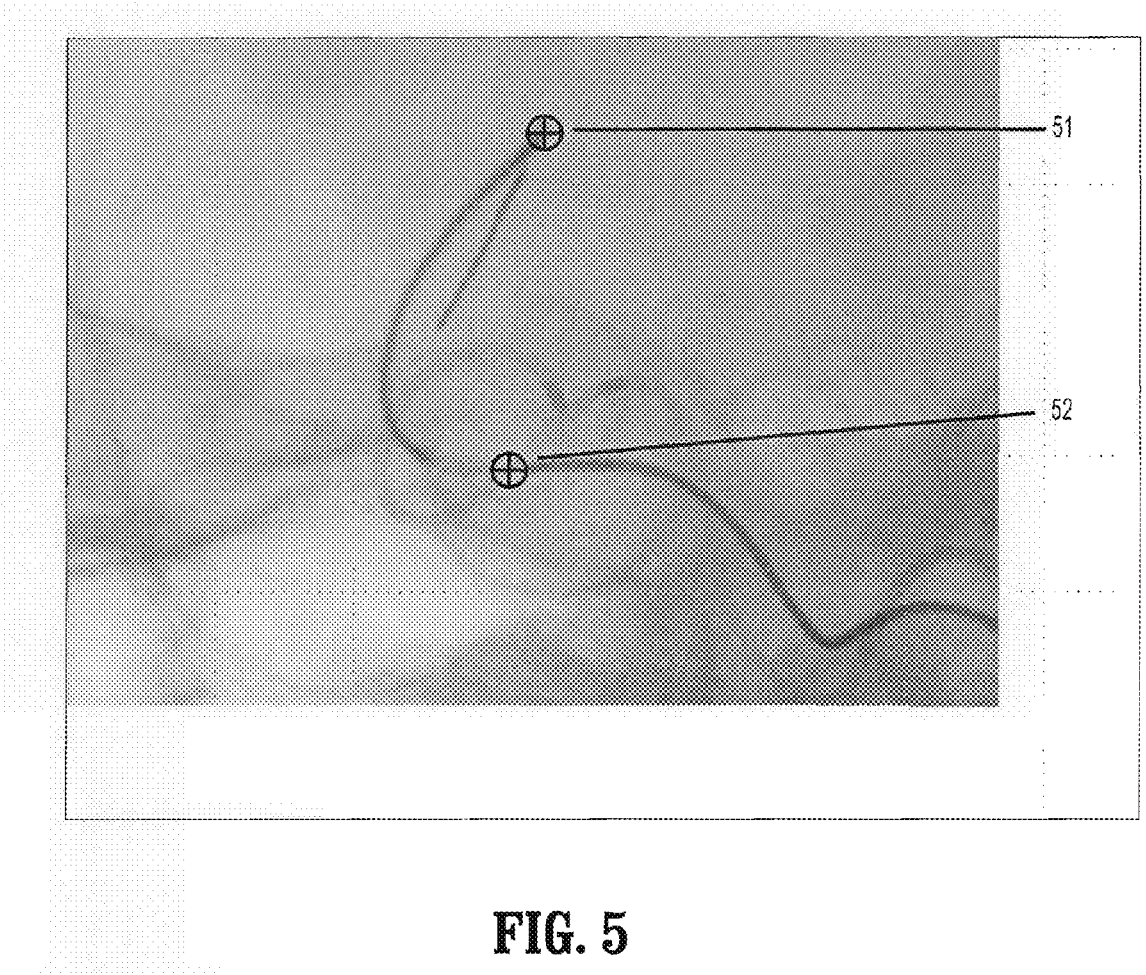
FIG. 5 illustrates exemplary stent end marker locations, according to an embodiment of the invention.

According to an embodiment of the invention, the planned stent end markers positions are superimposed on the combined fluoroscopic and roadmap image display inside the angiography suite control room. According to an embodiment of the invention, the target marker end locations are displayed in the shape of a cross hair surrounded by a circle. FIG. 5 illustrates exemplary stent end marker locations 51, 52. The diameter of this circle is slightly larger than the size of the end marker of a real stent. According to an embodiment of the invention, the diameter of the circle should be about 0.5 mm larger than the typical marker size for each stent on fluoroscopic images. The marker size information for each stent type is kept in lookup table in a computer file. However, embodiments of the invention are not limited to this end marker, and in other embodiments of the invention, the virtual end markers can be displayed in other shapes and forms. For example, another embodiment of the invention may display 2 lines perpendicular to the center line and extending the whole width of the planned stent. These lines could be 1 mm before and 1 mm after the planned virtual stent end markers location. In that case, the goal of doctor would be to place the real stent markers in between these two lines.

Some live monitors in the interventional suite are capable of displaying colors and others can only display gray scale colors. For the former, it is possible to superimpose the planned stent marker locations in a color such as the red color. For monitors only capable of displaying gray scale images, the planned stent marker locations can be superimposed in an intensity that is the inverse of that of the underlying intensity. For example, if the intensity of the pixel underlying the projected marker is $I_i$, then the intensity after overlaying the marker location is $$I_o = I_{max} + I_{min} - I_i,$$

where $I_{max}$ and $I_{min}$ are the minimum and maximum intensity values of the display monitor, respectively.

System Implementation

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 6:
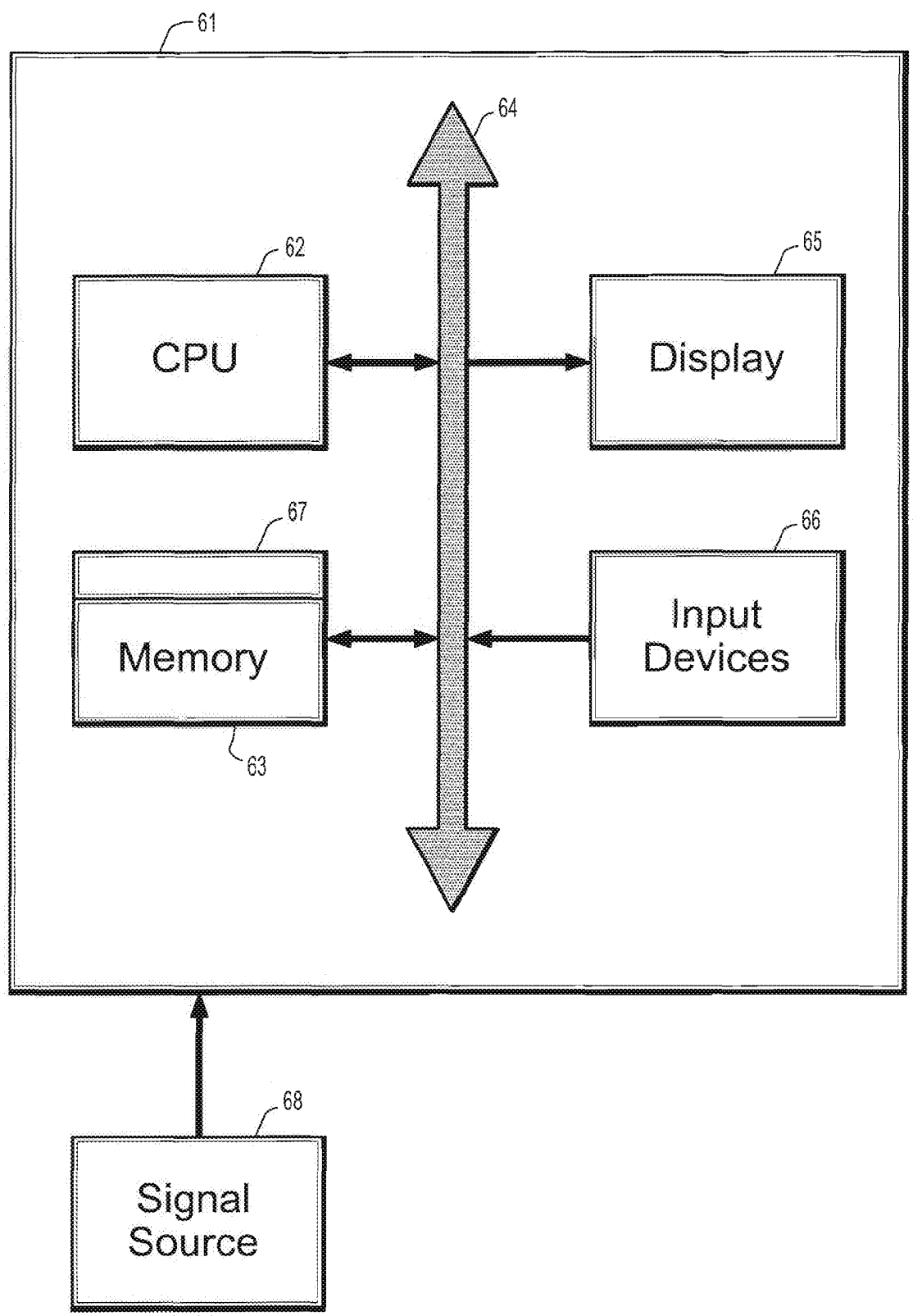
FIG. 6 is a block diagram of an exemplary computer system for implementing a method for intraoperative guidance of stent placement during endovascular interventions, according to an embodiment of the invention.

FIG. 6 is a block diagram of an exemplary computer system for implementing a method for intraoperative guidance of stent placement during endovascular interventions, according to an embodiment of the invention. Referring now to FIG. 6, a computer system 61 for implementing the present invention can comprise, inter alia, a central processing unit (CPU) 62, a memory 63 and an input/output (I/O) interface 64. The computer system 61 is generally coupled through the I/O interface 64 to a display 65 and various input devices 66 such as a mouse and a keyboard. The support circuits can include circuits such as cache, power supplies, clock circuits, and a communication bus. The memory 63 can include random access memory (RAM), read only memory (ROM), disk drive, tape drive, etc., or a combinations thereof. The present invention can be implemented as a routine 67 that is stored in memory 63 and executed by the CPU 62 to process the signal from the signal source 68. As such, the computer system 61 is a general purpose computer system that becomes a specific purpose computer system when executing the routine 67 of the present invention.

The computer system 61 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method for guiding stent deployment during an endovascular procedure, said method comprising the steps of:
constructing a 3-dimensional (3D) digital subtraction angiography (DSA) image of a target blood vessel lesion;
determining a length, diameter type, and placement location of a planned stent using said 3D DSA image;
creating a virtual model of said stent from said length, diameter type, and placement location of said planned stent;

overlaying an outline and shape of said planned stent on a 2-dimensional (2D) DSA image of said target lesion;

navigating a real stent to said target lesion by manipulating a stent deployment mechanism;

acquiring real-time 2D fluoroscopic images of said stent navigation, and projecting an image of said virtual model of said planned stent onto said fluoroscopic images, wherein 2D fluoroscopic images are acquired from a C-arm mounted X-ray apparatus; and deploying said real stent, when said real stent is aligned with said virtual model of said planned stent in said fluoroscopic images.

2. The method of claim 1, wherein said 3D DSA image is constructed from a plurality of 2D DSA images acquired at different orientations with respect to said target lesion.

3. The method of claim 1, further comprising repeating said steps of determining a length, diameter type, and placement location of a planned stent and overlaying an outline and shape of said planned stent on a 2D DSA image of said target lesion until the stent placement location is determined to be satisfactory, wherein the placement location and configuration of said planned stent in 3 dimensions is fully specified.

4. The method of claim 1, wherein said real stent includes radio-opaque end markers, and said virtual model of said planned stent includes virtual end markers that are projected onto said fluoroscopic images, wherein said real stent is aligned with said virtual model of said planned stent by aligning said real stent end markers with said virtual end markers.

5. The method of claim 1, further comprising updating said projection of said virtual model of said planned stent onto said fluoroscopic images whenever a new fluoroscopic image is acquired or whenever said C-arm is moved.

6. The method of claim 1, further comprising acquiring a 2D roadmap DSA image and overlaying said roadmap image on said fluoroscopic image, wherein said roadmap image aids in navigating said real stent to said target lesion.

7. The method of claim 1, wherein projecting an image of said virtual model of said planned stent onto said fluoroscopic images comprises representing said virtual model of said planned stent by a centerline and a plurality of spaced perpendicular lines whose length is about equal to a diameter of expansion of said real stent at a location of each said perpendicular line.

8. The method of claim 4, wherein said virtual end markers are represented by a cross hair surrounded by a circle, wherein a diameter of said circle is larger than the size of the real end marker.

9. A method for guiding stent deployment during an endovascular procedure, said method comprising the steps of:

providing a virtual stent model of a real stent that specifies a length, diameter, shape, and placement location of said real stent, wherein said real stent includes real radio-opaque end markers, and said virtual stent model includes virtual end markers that are projected onto fluoroscopic images;

projecting an outline and shape taken from said virtual stent model onto a 2-dimensional (2D) DSA image of a target lesion;

navigating a real stent to said target lesion by manipulating a stent deployment mechanism while simultaneously acquiring real-time 2D fluoroscopic images of said stent navigation, and overlaying each said fluoroscopic image on said 2D DSA image having said projected outline and shape, wherein said 2D fluoroscopic images are acquired from a C-arm mounted X-ray apparatus; and updating said projection of said outline and shape onto said fluoroscopic images whenever a new fluoroscopic image is acquired or whenever said C-arm is moved, wherein said real stent is aligned with said virtual stent model by aligning said real stent end markers with said virtual end markers.

10. The method of claim 9, wherein said virtual stent model is created using a 3-dimensional (3D) image of a target blood vessel lesion, and determining a length, diameter type, and placement location of a planned real stent using said 3D image.

11. The method of claim 10, wherein said 3D image of said target lesion is created by constructing a 3-dimensional (3D) digital subtraction angiography (DSA) image of said target blood vessel lesion, wherein said 3D DSA image is constructed from a plurality of 2D DSA images acquired at different orientations with respect to said target lesion.

12. The method of claim 10, wherein said 3D image of said target lesion is one of a magnetic resonance image and a computed tomography image, and further comprising registering said 3D image of said target lesion to a 3D DSA image of said target lesion.

13. The method of claim 9, wherein projecting said virtual stent model onto a 2D DSA image comprises determining 2D coordinates u, v of said virtual stent model in said 2D DSA image from an equation $$\begin{bmatrix} \alpha u \\ \alpha v \\ \alpha \end{bmatrix} = P \cdot \begin{bmatrix} x \\ y \\ z \\ 1 \end{bmatrix},$$

wherein and P is a 3×4 matrix with 10 degrees of freedom obtained from knowledge of design parameters of said C-arm, system calibration procedure, and a location of the C-arm, (x, y, z) is a point in said 3D image, and a is a scalar determined by specifying P and (x, y, z).

14. The method of claim 9, further comprising deploying said real stent, when said real stent is aligned with said virtual stent model in said fluoroscopic images.

15. The method of claim 9, wherein projecting said virtual stent model onto a 2D DSA image comprises representing said virtual stent model by a centerline and a plurality of spaced perpendicular lines whose length is about equal to a diameter of expansion of said real stent at a location of each said perpendicular line.

16. The method of claim 9, wherein an intensity $I_o$ of said projected virtual end marker is $I_o = I_{max} + I_{min} - I_i$, wherein $I_{max}$ and $I_{min}$ are the minimum and maximum intensity values of the display monitor, respectively, and $I_i$ is the intensity of the pixel underlying said projected virtual end marker.

17. A program storage device readable by a computer, tangibly embodying a program of instructions executable by the computer to perform the method steps for guiding stent deployment during an endovascular procedure, said method comprising the steps of:

providing a virtual stent model of a real stent that specifies a length, diameter, shape, and placement location of said real stent, wherein said real stent includes real radio-opaque end markers, and said virtual stent model includes virtual end markers that are projected onto fluoroscopic images;

projecting an outline and shape taken from said virtual stent model onto a 2-dimensional (2D) DSA image of a target lesion;

manipulating a stent deployment mechanism to navigate said real stent to said target lesion while simultaneously acquiring real-time 2D fluoroscopic images of said stent navigation, and overlaying each said fluoroscopic image on said 2D DSA image having said projected outline and shape, wherein said 2D fluoroscopic images are acquired from a C-arm mounted X-ray apparatus; and updating said projection of said outline and shape onto said fluoroscopic images whenever a new fluoroscopic image is acquired or whenever said C-arm is moved, wherein said real stent is aligned with said virtual stent model by aligning said real stent end markers with said virtual end markers.

18. The computer readable program storage device of claim 17, wherein said virtual stent model is created using a 3-dimensional (3D) image of a target blood vessel lesion, and determining a length, diameter type, and placement location of a planned real stent using said 3D image.

19. The computer readable program storage device of claim 18, wherein said 3D image of said target lesion is created by constructing a 3-dimensional (3D) digital subtraction angiography (DSA) image of said target blood vessel lesion, wherein said 3D DSA image is constructed from a plurality of 2D DSA images acquired at different orientations with respect to said target lesion.

20. The computer readable program storage device of claim 18, wherein said 3D image of said target lesion is one of a magnetic resonance image and a computed tomography image, and further comprising registering said 3D image of said target lesion to a 3D DSA image of said target lesion.

21. The computer readable program storage device of claim 17, wherein projecting said virtual stent model onto a 2D DSA image comprises determining 2D coordinates u, v of said virtual stent model in said 2D DSA image from an equation $$\begin{bmatrix} \alpha u \\ \alpha v \\ \alpha \end{bmatrix} = P \cdot \begin{bmatrix} x \\ y \\ z \\ 1 \end{bmatrix},$$

wherein and P is a 3×4 matrix with 10 degrees of freedom obtained from knowledge of design parameters of said C-arm, system calibration procedure, and a location of the C-arm, (x, y, z) is a point in said 3D image, and a is a scalar determined by specifying P and (x, y, z).

22. The computer readable program storage device of claim 17, the method further comprising deploying said real stent, when said real stent is aligned with said virtual stent model in said fluoroscopic images.

23. The computer readable program storage device of claim 17, wherein projecting said virtual stent model onto a 2D DSA image comprises representing said virtual stent model by a centerline and a plurality of spaced perpendicular lines whose length is about equal to a diameter of expansion of said real stent at a location of each said perpendicular line.

24. The computer readable program storage device of claim 17, wherein an intensity $I_o$ of said projected virtual end marker is $I_o = I_{max} + I_{min} - I_i$, wherein $I_{max}$ and $I_{min}$ are the minimum and maximum intensity values of the display monitor, respectively, and $I_i$ is the intensity of the pixel underlying said projected virtual end marker.

* * * * *